(12) United States Patent
Lin et al.

(10) Patent No.: US 6,648,960 B1
(45) Date of Patent: Nov. 18, 2003

(54) METHOD OF SHORTENING A WORKING AND SETTING TIME OF A CALCIUM PHOSPHATE CEMENT (CPC) PASTE

(75) Inventors: Jiin-Huey Chern Lin, Winnetka, IL (US); Chien-Ping Ju, Carbondale, IL (US); Kuan-Liang Lin, Fengyuan (TW); Chih-Hung Tsai, Taichung (TW); I-Chang Wang, Tainan (TW); Wen-Cheng Chen, Tainan (TW)

(73) Assignee: Cana Lab Corporation, Taipei (TW)

( * ) Notice: Subject to any disclaimer, the term of this patent is extended or adjusted under 35 U.S.C. 154(b) by 0 days.

(21) Appl. No.: 10/179,879

(22) Filed: Jun. 26, 2002

(51) Int. Cl.[7] ............................................... C04B 12/02
(52) U.S. Cl. ...................... 106/690; 106/691; 423/314; 423/315
(58) Field of Search .................................. 106/690, 691; 423/314, 315

(56) References Cited

U.S. PATENT DOCUMENTS 6,379,453 B1 * 4/2002 Lin et al. ..................... 106/690

FOREIGN PATENT DOCUMENTS

| JP | 2000169200 | * | 6/2000 |
| JP | 2001259013 | * | 9/2001 |

* cited by examiner

*Primary Examiner*—Paul Marcantoni
(74) *Attorney, Agent, or Firm*—Bacon & Thomas

(57) ABSTRACT

A method of shortening a working and setting time of a CPC paste without using additives or sacrificing its strength, which includes heating CPC powder so that the CPC powder is maintained at a temperature of 50–400° C. for a period of time which is greater than one minute.

20 Claims, 5 Drawing Sheets

US 6,648,960 B1

METHOD OF SHORTENING A WORKING AND SETTING TIME OF A CALCIUM PHOSPHATE CEMENT (CPC) PASTE

FIELD OF THE INVENTION

The present invention is related to a calcium phosphate cement (CPC), and in particular to a method of shortening a working and setting time of a CPC paste.

BACKGROUND OF THE INVENTION

As early as 1983 Brown and Chow have indicated that mixture of tetracalcium phosphate (TTCP) and dicalcium phosphate anhydrous (DCPA) powders in a diluted phosphate-containing solution led to the formation of hydroxyapatite (HA). According to this chemical reaction a calcium phosphate cement (CPC) was first developed and patented in 1986 [U.S. Pat. No. 4,612,053]. Thereafter, using this moldable CPC paste as bone substitute has brought a great deal of attention to the researchers and industry in this field and a variety of fabrication methods have been proposed.

One major advantage of CPC over calcium phosphate blocks or granules is that CPC paste can be molded to any desirable shape during operation. The paste hardens in-situ with HA as its main final constituent. By adjusting viscosity of the CPC paste, CPC paste is injectable using a surgical syringe that finds many applications for orthopedic, craniofacial and periodontal operations.

Yet there are still problems during practical application of CPC paste, at least including its prolong setting time and dispersion upon early contact with blood or aqueous media. Appropriate working/setting time is critical for surgical applications. Ideally a CPC paste should be applied when it is still workable and wound may be closed after the cement is set. Appropriate working times have been suggested not to be much longer than 8 min for orthopedic applications.

Different approaches were reported to shorten the setting time of CPC paste. Examples include increasing phosphate hardening solution concentration, using different hardening solutions, and mixing in calcium phosphate powders with such additives as HA, CaO, $Na_2O$, $P_2O_5$, MgO, $CaF_2$ and collagen. Nevertheless, these modifications are often accompanied with sacrifices in biocompatibility and/or mechanical strength.

SUMMARY OF THE INVENTION

A primary objective of the present invention is to provide a method of shortening a working and setting time of a CPC paste, which is accomplished by subjecting the CPC powder to a heat treatment without using additives or sacrificing its strength.

DETAILED DESCRIPTION OF THE INVENTION

Figure 1:
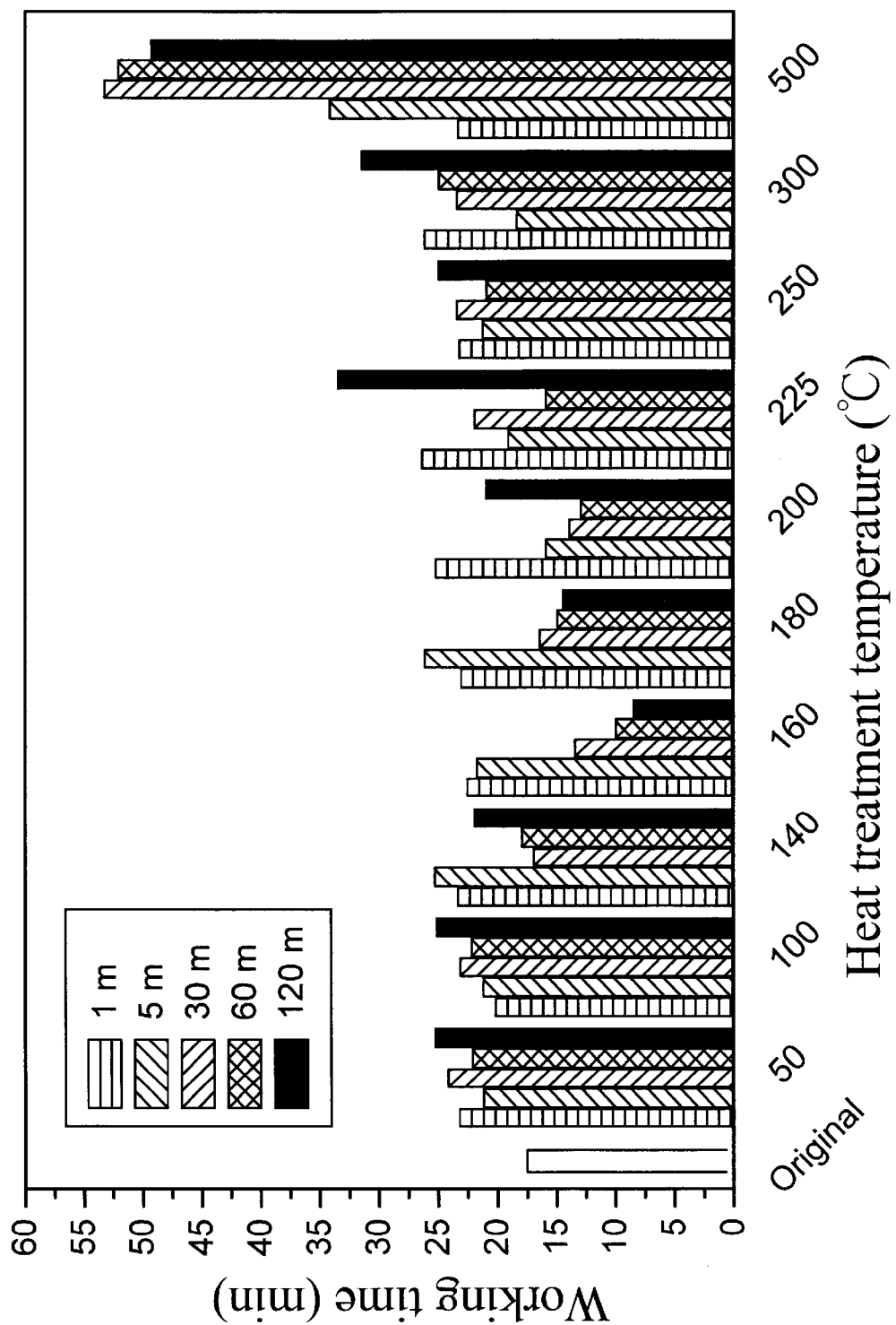
FIG. 1 is a plot showing the effect of heat treatment on the working time of the CPC paste.

The present invention provides a method of shortening a working and setting time of a calcium phosphate cement (CPC) paste formed by mixing a CPC powder with an aqueous solution, said method comprising heating said CPC powder, prior to said mixing, so that said CPC powder is maintained at a temperature of 50–400° C. for a period of time which is greater than one minute, and that a CPC paste formed by mixing the resulting heated CPC powder with said aqueous solution has a shortened working and setting time in comparison with that formed by mixing said CPC powder not subjected to said heating with said aqueous solution.

Preferably, said temperature is 100–250° C., and said period of time is less than 240 minutes. More preferably, said temperature is 160–200° C., and said period of time is ranging from 30 minutes to 1.20 minutes.

A CPC powder suitable for use in the method of the present invention includes (but not limited to) one or more calcium phosphates selected from the group consisting of alpha-tricalcium phosphate (α-TCP), beta- tricalcium phosphate (β-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium polyphosphate, calcium metaphosphate, anhydrous tricalcium phosphate, tricalcium phosphate hydrate, apatite, hydroxyapatite, and fluorapatite. Preferably, said CPC powder comprises dicalcium phosphate anhydrous and tetracalcium phosphate.

Preferably, said CPC powder has particle sizes ranging from 0.05 to 100 microns, and particles of said CPC powder have whiskers or fine crystals on their surfaces having a width ranging from 1 to 100 nm and a length ranging from 1 to 1000 nm. Details of the preparation of the CPC having whiskers or fine crystals on the surfaces of the CPC particles can be found in EP 1172076 A (January 2002), which is incorporated herein by reference.

Preferably, said CPC powder has a molar ratio of calcium to phosphate ranging from 0.5 to 2.5.

EXAMPLE 1

To fabricate the CPC, the TTCP ($Ca_4(PO_4)_2O$)powder was prepared from the reaction of dicalcium pyrophosphate ($Ca_2P_2O_7$) (Sigma Chem. Co., St Louis, Mo., USA) and calcium carbonate ($CaCO_3$) (Katayama Chem. Co., Tokyo, Japan) using the method suggested by Brown and Epstein [*Journal of Research of the National Bureau of standards—A Physics and Chemistry* 6 (1965) 69A 12], while the DCPA ($CaHPO_4$) powder is a commercial product (Jassen Chemical Co., Japan). Through a special pre-treatment process on the mixture of the original TTCP and DCPA powders prior to mixing with the phosphate-containing solution, whiskers or fine crystals were formed on the surfaces of the particles, so that the pre-treated mixture of the TTCP and DCPA powders had a capability to set in situ in an aqueous environment with sufficient strength to prevent dispersion. The pre-treatment process included mixing 5 g of a mixed TTCP/DCPA powder (1:1 in molar ratio) with 1.6 ml of 25 mM phosphorus acid aqueous solution by one-minute stirring, heating the resulting mixture in an oven at 50° C. for 30 minutes to dry the mixture, separately grinding the dried mixture for 20 minutes and for 5 minutes, and mixing the resulting particles of two different levels of grinding in 1:1 weight ratio.

To show heat treatment effect on working/setting time and compressive strength, the pre-treated CPC of mixed TTCP/DCPA powders (1:1 in molar ratio) were heat-treated in an air furnace (N 7/H, Nabertherm®, Germany). A series of heat treatment temperature (50–500° C.) and times (one min–one week) were selected, wherein 5 g of the CPC powder was placed in a 7.5 ml glass container, and the CPC/container were placed in the pre-heated air furnace at a pre-set temperature for a pre-determined time.

The heat-treated CPC powder was mixed with IM phosphate hardening solution having a pH value of 5.6 and in a liquid/powder ratio of 0.4 ml/gm. One minute after mixing, the paste was tested every 30 seconds to determine the working time and the setting time. Working time of the CPC was determined as the duration when the paste was no longer moldable, while setting time was measured according to ISO 1566 standard for zinc phosphate dental cements. The cement is considered set when a 400 gm weight loaded onto a Vical needle with a 1 mm diameter tip fails to make a perceptible circular indentation on the surface of the cement. During measurement the cement was kept in 60–70% relative humidity environment at 37° C.

One minute after mixing, the CPC paste was packed under a popularly-used pressure of 0.7 MPa for 15 min in a 6 mm diameter, 12 mm deep cylindrical stainless steel mold, the molded cylindrical CPC sample was removed from the mold, and was allowed to set before conducting compressive strength testing. The compressive strength was measured using a desk-top mechanical tester (Shimadzu AGS-500D, Tokyo, Japan) at a crosshead speed of 1.0 mm/min. To study immersion effect on compressive strength, CPC samples were immersed in Hanks' physiological solution that was maintained at 37° C. and agitated daily to help maintain uniform ion concentrations.

Figure 2:
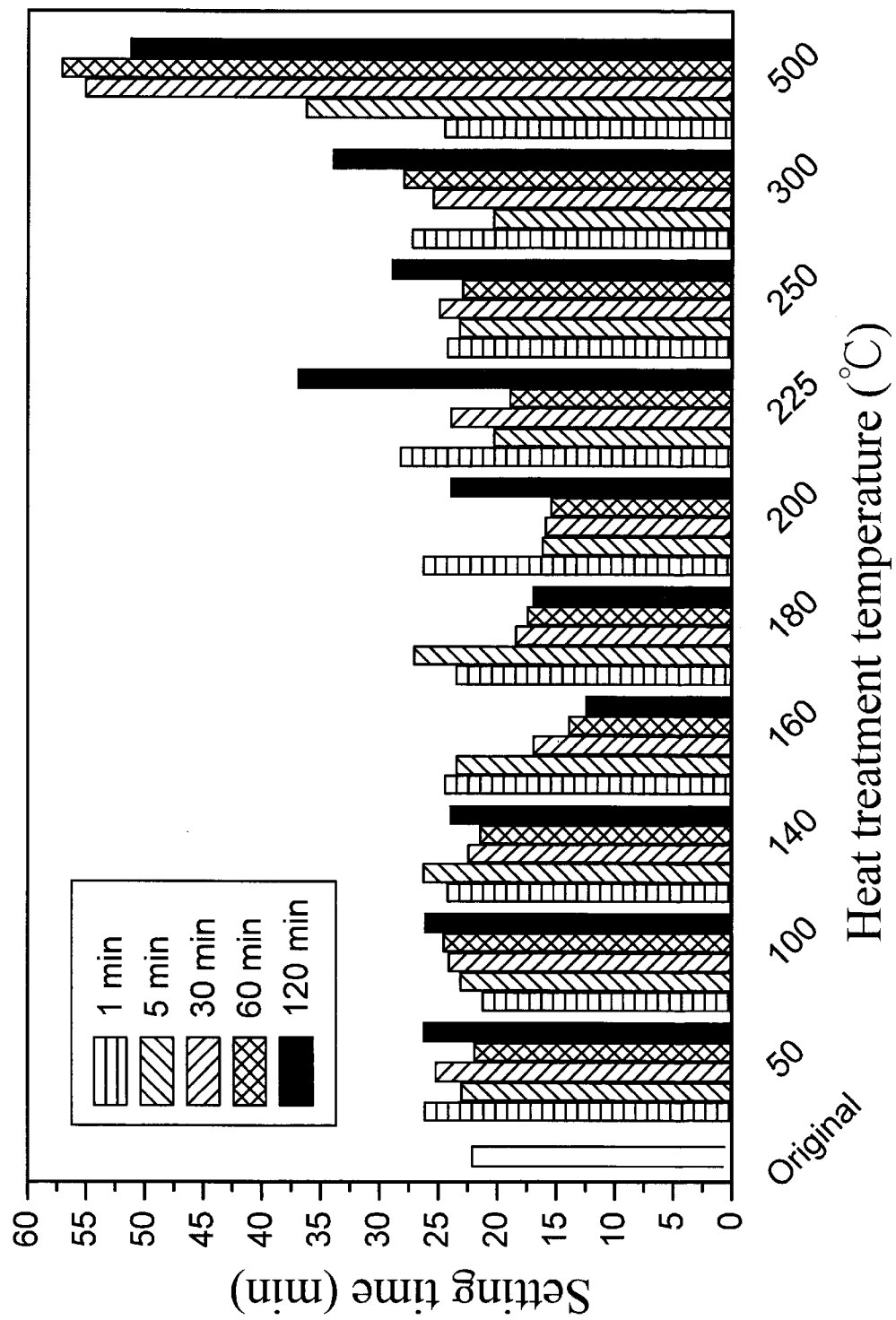
FIG. 2 is a plot showing the effect of heat treatment on the setting time of the CPC paste.

As indicated in FIGS. 1 and 2, the working/setting time of the CPC could be significantly changed by the present heat treatment. The working/setting time might increase or decrease, depending on heat treatment condition. In general, when the heat treatment temperature was too low or too high, the working/setting time became longer than that of original, untreated CPC. For example, when the CPC was heat-treated at 50° C. for even only 1 min, its working and setting times increased from 16.5 to 23.5 min and from 20.0 to 26.0 min, respectively. In the other extreme, when the CPC was heated at 500° C. for 120 min, its working and setting times increased to 49.5 and 51.5 min, respectively. A longer heat treatment time could prolong or shorten the working/setting time, depending on the temperature.

It is interesting to note that, when the CPC was treated for appropriate time at temperatures between about 160 and 200° C., its working/setting time was shortened. The most dramatic change was found in CPC heat-treated at 160° C. for 30–120 min, where its working and setting times largely decreased to 13.5–8.5 min and 17.0–12.5 min, respectively. Such working/setting times would be appropriate for orthopedic applications.

In two additional embodiments by using heat treatments under 160° C., 240 min; and 160° C., 480 min, the working time and setting time of the former are 10.0 min and 11.4 min; and for the latter are 14.1 min and 15.8 min. Compared to the results of the 160° C., 120 min case, a longer heat treatment is not advantageous.

Figure 3:
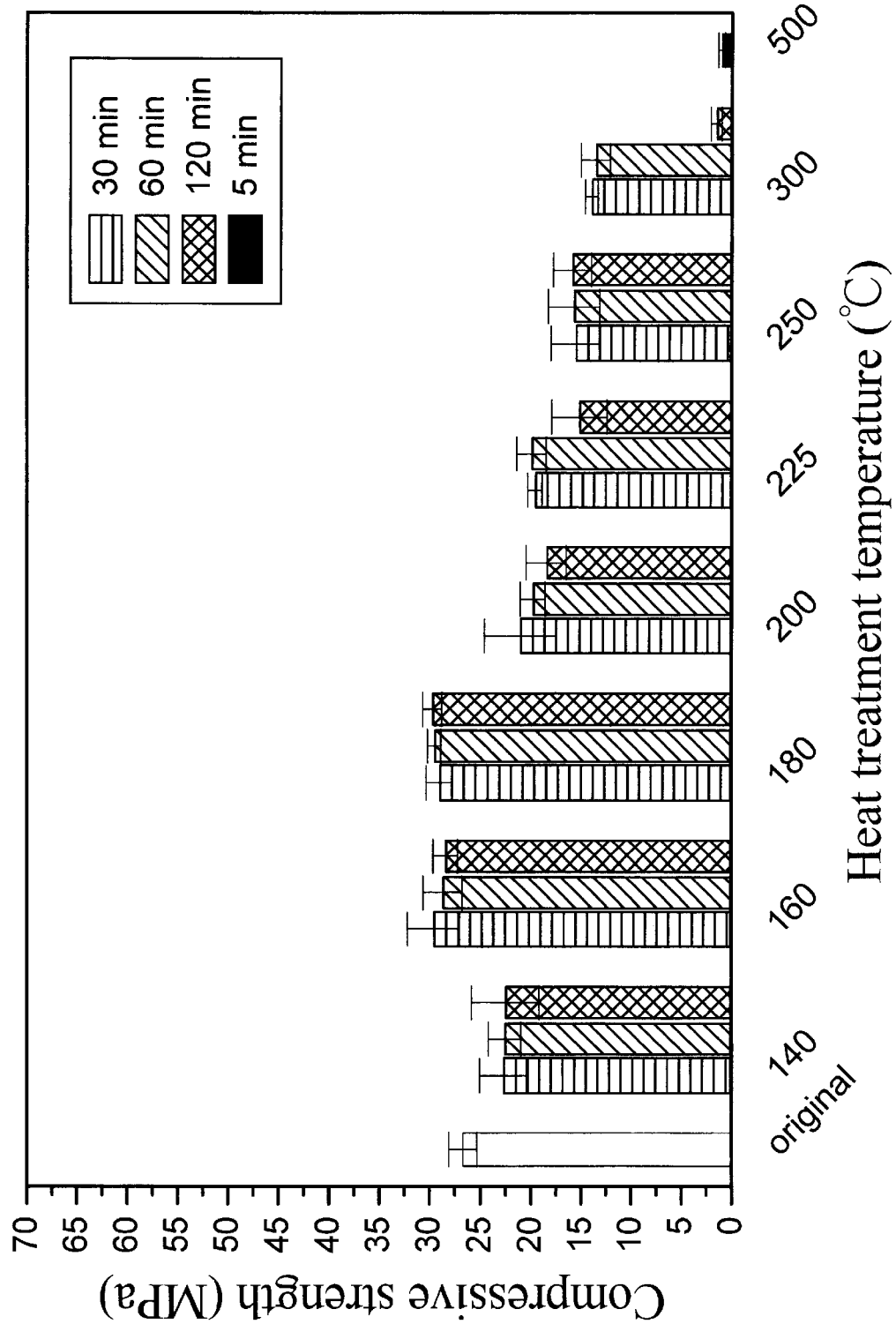
FIG. 3 is a plot showing the effect of heat treatment on the compressive strength of the molded CPC cylinder immersed in 37° C. Hanks' solution for 20 min.
Figure 4:
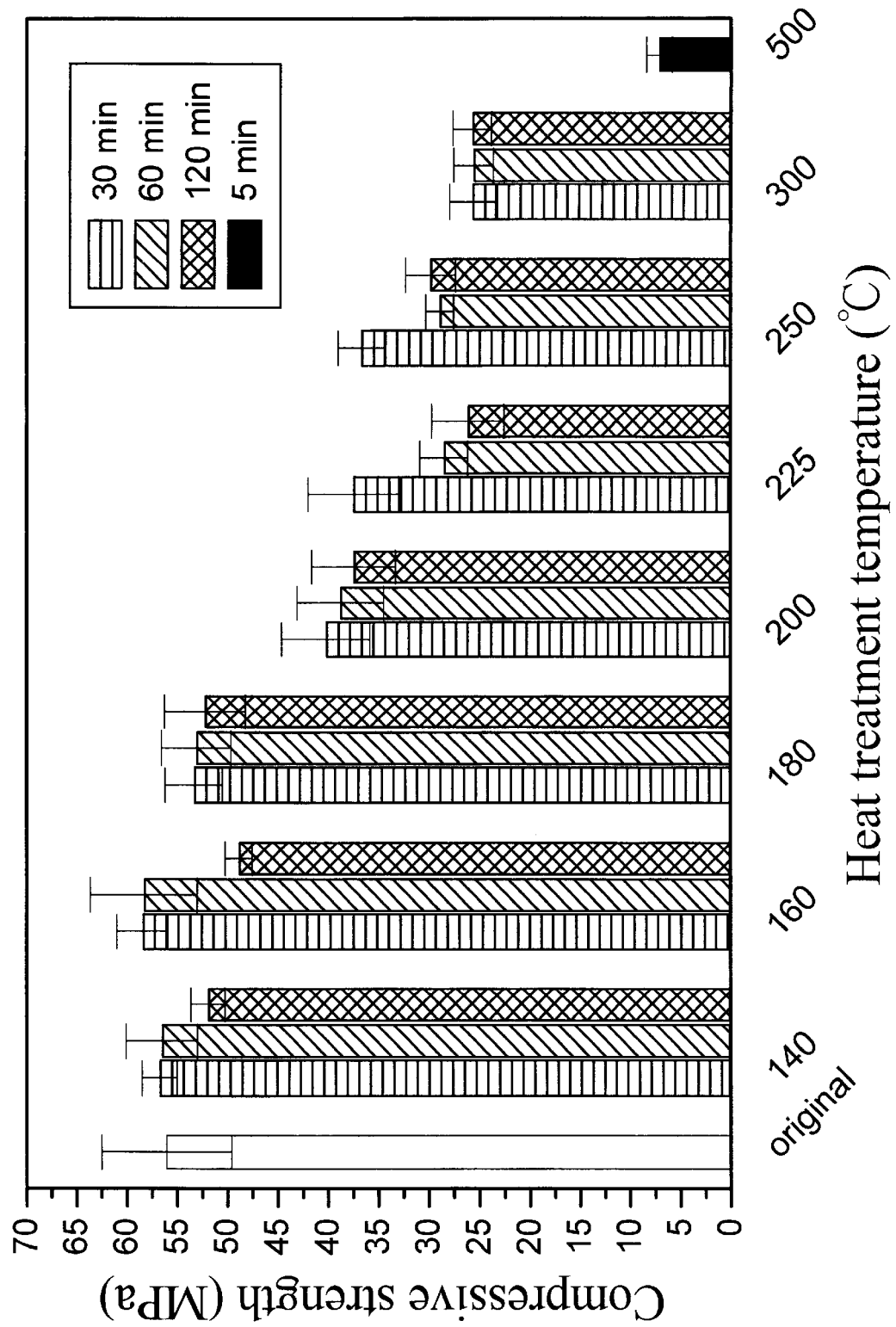
FIG. 4 is a plot showing the effect of heat treatment on the compressive strength of the molded CPC cylinder immersed in 37° C. Hanks' solution for one day.
Figure 5:
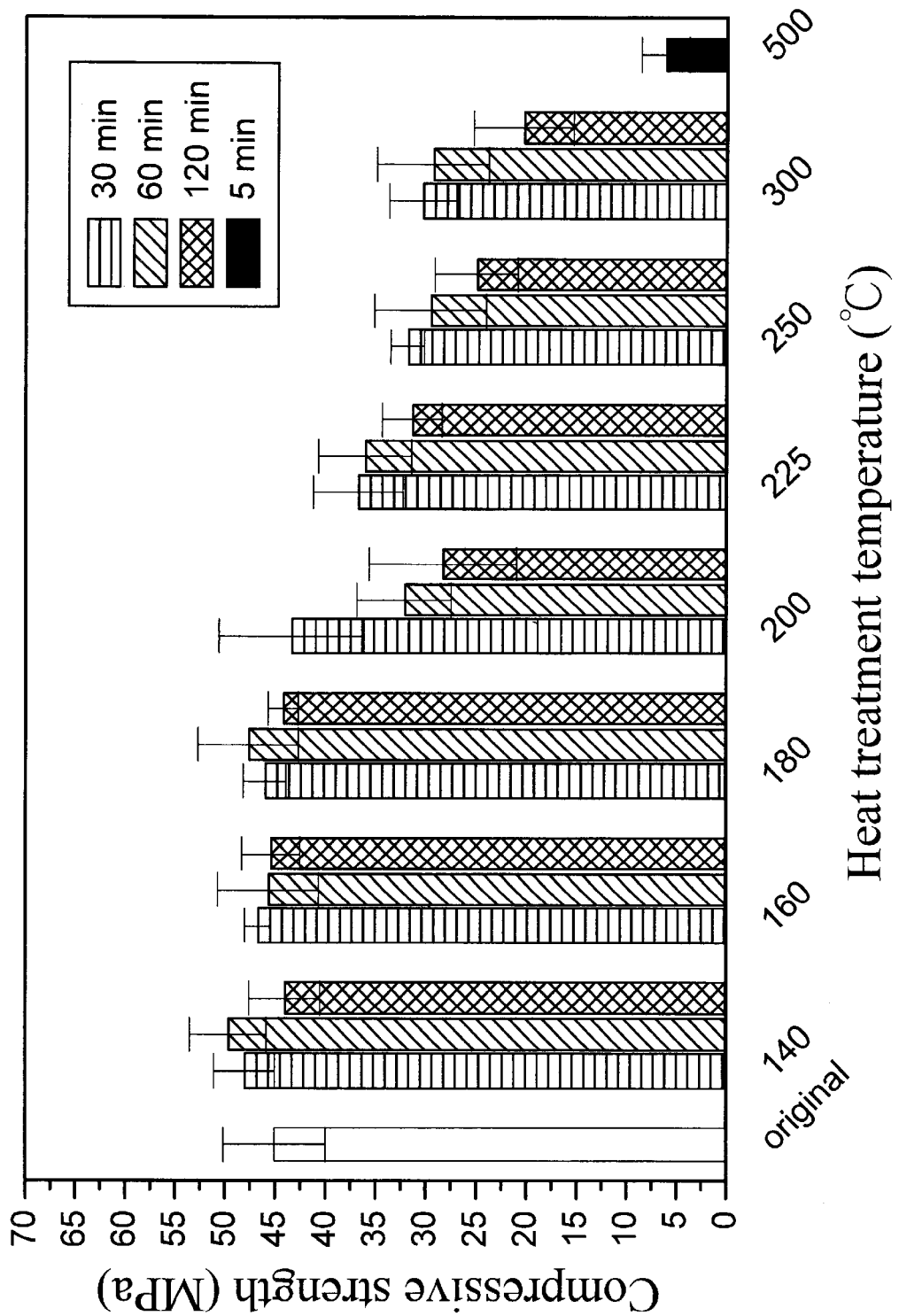
FIG. 5 is a plot showing the effect of heat treatment on the compressive strength of the molded CPC cylinder immersed in 37° C. Hanks' solution for 7 days.

Since short term (typically within 30 min) and long term strengths are both important for CPC (especially for load-bearing applications), the compressive strengths of CPC immersed in Hanks' solution for 20 min, 1 day and 7 days were measured. As indicated in FIGS. 3–5, the highest 20-min compressive strengths were obtained from CPC heat-treated at 160 or 180° C. When treated at other temperatures, the strength became lower than that of untreated CPC. Except 140° C., the compressive strength generally decreased with temperature. The data of CPC treated at 500° C. for 30 min or longer were not included in these figures due to their near-zero values.

It can be seen from data shown in FIGS. 1 to 5 that, while the strengths of immersed CPC treated at lower temperatures (<180° C.) were not much different from that of untreated one, their working/setting times could be much different (FIGS. 1 and 2). For example, the strength of immersed CPC treated at 160° C. for 60 min was similar to that of untreated CPC, yet its working time (10.0 min) and setting time (14.0 min) were respectively much shorter than the working time (16.5 min) and setting time (20.0 min) of untreated CPC. The heat treatment as shown in these examples provides a simple approach that can largely reduce the working/setting time of CPC without using any additives or sacrificing its strength.

EXAMPLE 2

The procedures of Example 1 were repeated except that the CPC powder used was a mixed TTCP/DCPA powder (1:1 in molar ratio) without being subjected to the pre-treatment process. The results are shown in Table 1.

TABLE 1

| Heat treatment | Working time (min) | Setting time (min) |
|---|---|---|
| Original | 19.7 | 21.2 |
| 150° C., 60 min | 15.7 | 17.5. |
| 200° C., 30 min | 17.5 | 18.2 |
| 200° C., 60 min | 9.2 | 10.7 |
| 200° C., 120 min | 10.3 | 13.7 |

It can be seen from Table 1 that significantly reduced working time and setting time are observed when the CPC powder is subjected to a heat treatment of 200° C. for 60–120 min.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of shortening a working and setting time of a calcium phosphate cement (CPC) paste formed by mixing a CPC powder with an aqueous solution, said method comprising heating said CPC powder, prior to said mixing, so that said CPC powder is maintained at a temperature of 50–400° C. for a period of time which is greater than one minute, and that a CPC paste formed by mixing the resulting heated CPC powder with said aqueous solution has a shortened working and setting time in comparison with that formed by mixing said CPC powder not subjected to said heating with said aqueous solution.

2. The method according to claim 1, wherein said temperature is 100–250° C., and said period of time is less than 240 minutes.

3. The method according to claim 2, wherein said temperature is 160–200° C., and said period of time is ranging from 30 minutes to 120 minutes.

4. The method according to claim 1, wherein said CPC powder comprises one or more calcium phosphates selected from the group consisting of alpha-tricalcium phosphate (α-TCP), beta- tricalcium phosphate (β-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium polyphosphate, calcium metaphosphate, anhydrous tricalcium phosphate, tricalcium phosphate hydrate, apatite, hydroxyapatite, and fluorapatite.

5. The method according to claim 1, wherein said CPC powder comprises dicalcium phosphate anhydrous and tetracalcium phosphate.

6. The method according to claim 2, wherein said CPC powder comprises dicalcium phosphate anhydrous and tetracalcium phosphate.

7. The method according to claim 3, wherein said CPC powder comprises dicalcium phosphate anhydrous and tetracalcium phosphate.

8. The method according to claim 1, wherein said CPC powder has particle sizes ranging from 0.05 to 100 microns, and particles of said CPC powder have whiskers or fine crystals on their surfaces having a width ranging from 1 to 100 nm and a length ranging from 1 to 1000 nm.

9. The method according to claim 1, wherein said CPC powder has a molar ratio of calcium to phosphate ranging from 0.5 to 2.5.

10. The method according to claim 8, wherein said CPC powder comprises dicalcium phosphate anhydrous and tetracalcium phosphate.

11. A method of preparing a calcium phosphate cement (CPC) paste comprising mixing a CPC powder with an aqueous solution, and heating said CPC powder, prior to said mixing, so that said CPC powder is maintained at a temperature 50–400° C. for a period of time which is greater than one minute, and that a CPC paste formed by mixing the resulting heated CPC powder with said aqueous solution has a shortened working and setting time in comparison with that formed by mixing said CPC powder not subjected to said heating with said aqueous solution.

12. A method for preparing a calcium phosphate cement (CPC) paste which comprises heating a CPC powder at a temperature of from 50–400° C. for a period of time which is greater than one minute, and then mixing the heated CPC powder with an aqueous solution to for a CPC paste, said paste having a shortened working and setting time in comparison with a paste formed by mixing the CPC powder not subjected to heating prior to mixing with the aqueous solution.

13. The method according to claim 12, wherein said temperature is 100–250° C., and said period of time is less than 240 minutes.

14. The method according to claim 12, wherein said CPC powder comprises one or more calcium phosphates selected from the group consisting of alpha-tricalcium phosphate (α-TCP), beta- tricalcium phosphate (β-TCP), tetracalcium Sa, phosphate (TTCP), monocalcium phosphate monohydate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium polyphosphate, calcium metaphosphate, anhydrous tricalcium phosphate, tricalcium phosphate hydrate, apatite, hydroxyapatite, and fluoroaptite.

15. The method according to claim 12, wherein said CPC powder comprises dicalcium phosphate anhydrous and tetracalcium phosphate.

16. The method according to claim 13, wherein said CPC powder comprises dicalcium phosphate anhydrous and tetracalcium phosphate.

17. The method according to claim 13, wherein said CPC powder comprises dicalcium phosphate anhydrous and tetracalcium phosphate, and wherein the temperature is 160–200° C., and said period of time is from 30 to 120 minutes.

18. The method according to claim 12, wherein said CPC powder has particle sizes ranging from 0.05 to 100 microns, and particles of said CPC powder have whiskers or fine crystals on their surfaces having a width ranging from 1 to 100 nm and a length ranging from 1 to 1000 nm.

19. The method according to claim 12, wherein said CPC powder has a molar ratio of calcium to phosphate ranging from 0.5 to 2.5.

20. The method according to claim 18, wherein said CPC powder comprises dicalcium phosphate anhydrous and tetracalcium phosphate.

* * * * *